United States Patent [19]

Hofmann

[11] Patent Number: Plant 7,080

[45] Date of Patent: Dec. 19, 1989

[54] DISTINCT VARIETY OF GERANIUM PLANT NAMED ISABELL

[75] Inventor: Christa Hofmann, Dresden, German Democratic Rep.

[73] Assignee: Oglevee Ltd., Connellsville, Pa.

[21] Appl. No.: 298,512

[22] Filed: Jan. 18, 1989

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

A new geranium cultivar is distinguished by its self-branching upright plant of excellent conformation. A dark green foliage compliments its brilliant scarlet bloom color. The numerous longlasting, non-shattering flower clusters place this plant well beyond the current varieties in this color class.

1 Drawing Sheet

BACKGROUND OF THE NEW PLANT

The present invention comprises a new and distinct cultivar of Pelargonium hortorum bailey known by the varietal name of Isabell. The new variety was discovered in a selective breeding program by Mrs. Christa Hofmann and is a selection from the inbreeding of "Dresdner Rubin" and selections of "Hannchen Ander," "Fritz Ander" and "Bruni" (commercialized in the United States as Glacier Crimson and U.S. Plant Pat. No. 5,057).

The new cultivar was discovered in the year 1981 in the VEB Saatzucht Zierpflanzen Dresden, German Democratic Republic, and has been repeatedly asexually reproduced by cuttings over a two year-period for Oglevee Associates, Inc. in Connellsville, Pa. It has been trial and field tested during the summers of 1987 and 1988. It has been found to retain its distinctive characteristics through successive propagations.

The new cultivar, when grown in a greenhouse in Connellsville, Pa., using natural light and 60° F. night temperature, 68° F. day temperature and 71° F. vent temperature, has a response time of eight weeks from a well-rooted cutting to a flowering plant in a four inch (10 cm) pot.

DESCRIPTION OF THE DRAWING

The accompanying photographic drawing illustrates a new cultivar, the color being as nearly true as possible with color illustrations of this type.

DESCRIPTION OF THE NEW PLANT

The following detailed descriptions set forth the characteristics of the new cultivar. The data which define these characteristics were collected from asexual reproductions carried out for Oglevee Associates, Inc., in Connellsville, Pa. The plant history was taken on eight-week plants, blossomed under natural light in a greenhouse, and color readings were taken indoors under 200–220 foot candles of cool white fluorescent light. The plants were rooted on Aug. 4, 1987, and flowered Sept. 20, 1987 in a soilless media with a constant fertilizer feed of 250–275 parts per million nitrogen and potassium. Color references are primarily to the R.H.S. Colour Chart of The Royal Horticultural Society of London.

THE PLANT

Classification:

*Botanical.*—*Pelargonium* × *hortorum* bailey.

*Commercial.*—Zona geranium.

Form: Bush. Basal branching, free and early flowering, upright habit.

Height: 25.0–30.0 cm from the media surface.

Growth: Free-branching from base; medium internode length.

Strength: Stands upright without artificial support.

Foliage: Large leaves with zonation.

Leaves:

*Size.*—8.0–10.0 cm wide.

*Shape.*—Reniform, cordate base.

*Margin.*—Crenate.

*Texture.*—Downy; dull, not reflective.

*Color.*—Outside margin, Green group 137B; center, Green group 137C.

*Zonation.*—Greyed-purple group 187C.

*Ribs and veins.*—Palmate. veination, Yellow-green group 145B.

Petioles: Stalked petiole; 8.0–12.0 cm, Green group 137C.

Stem:

*Color.*—Yellow-green group 146B.

*Internodes.*—2.0–4.0 cm between nodes.

THE BUD

Shape: Umbel formed with approximately 20–25 flower buds.

Color: When petals protrude from the bud, they appear Red group 51B. As the petals mature, they become Red group 43A but with more intensity.

INFLORESCENCE

Blooming habit: Continuous, upright, semi-double, hemispherical in shape.

Size: 10.0–15.0 cm across.

Borne: Umbel, florets on pedicel, pedicel on peduncle; 10.0–15.0 cm above foliage.

Florets:

*Form.*—Flat with petaloids.

*Color.*—Top — Red group 40A. Bottom — Red group 43B.

*Petals.*—5–7 separate — not united; margin entire obovate; palmate veination; smooth, flat Red group 40A.

*Size.*—4.0–6.0 cm wide.

*Texture and tonality.*—Smooth; color from a distance appears fluorescent with bright scarlet bloom on top of a bushy, medium green foliage.

Petaloids:

*Quantity.*—0–3.

*Shape.*—Narrow, elongated, twisted.

*Color.*—Red group 40A.

Pedicel:

*Length.*—45.0–55.0 cm in length.

*Color.*—Apical end color — Red group 46A; basal end color — Yellow-green group 146C.

Peduncle: Arises from node, opposite leaf petiole; 14.0–18.0 cm in length.

REPRODUCTIVE ORGANS

Stamens:

*Anthers.*—Elliptical; 1.0–2.0 mm.

*Filaments.*—5.0 mm in length.

*Pollen.*—Golden Brown.

Pistils:

*Number.*—1 with 5 parted stigma.

*Length.*—0.5–0.9 cm in length.

*Stigma.*—5 parted, curls toward ovary.

*Style.* 1; 3.0 mm in length.

Ovaries: 5.0 mm in length; pubescent, superior.

Fruit: None observed.

The new cultivar is characterized by its self-branching, upright plant of excellent conformation. The dark green foliage compliments the brilliant scarlet bloom color. The numerous longlasting, non-shattering flower clusters exceed the existing varieties in this color class. It is a more vigorous plant than Glacier Crimson but still has the neat, bushy habit.

I claim:

1. A new and distinct variety of geranium plant characterized by a self-branching, upright plant of excellent conformation, a dark green foliage with a scarlet bloom color, and numerous longlasting, non-shattering flower clusters substantially as herein shown and described.

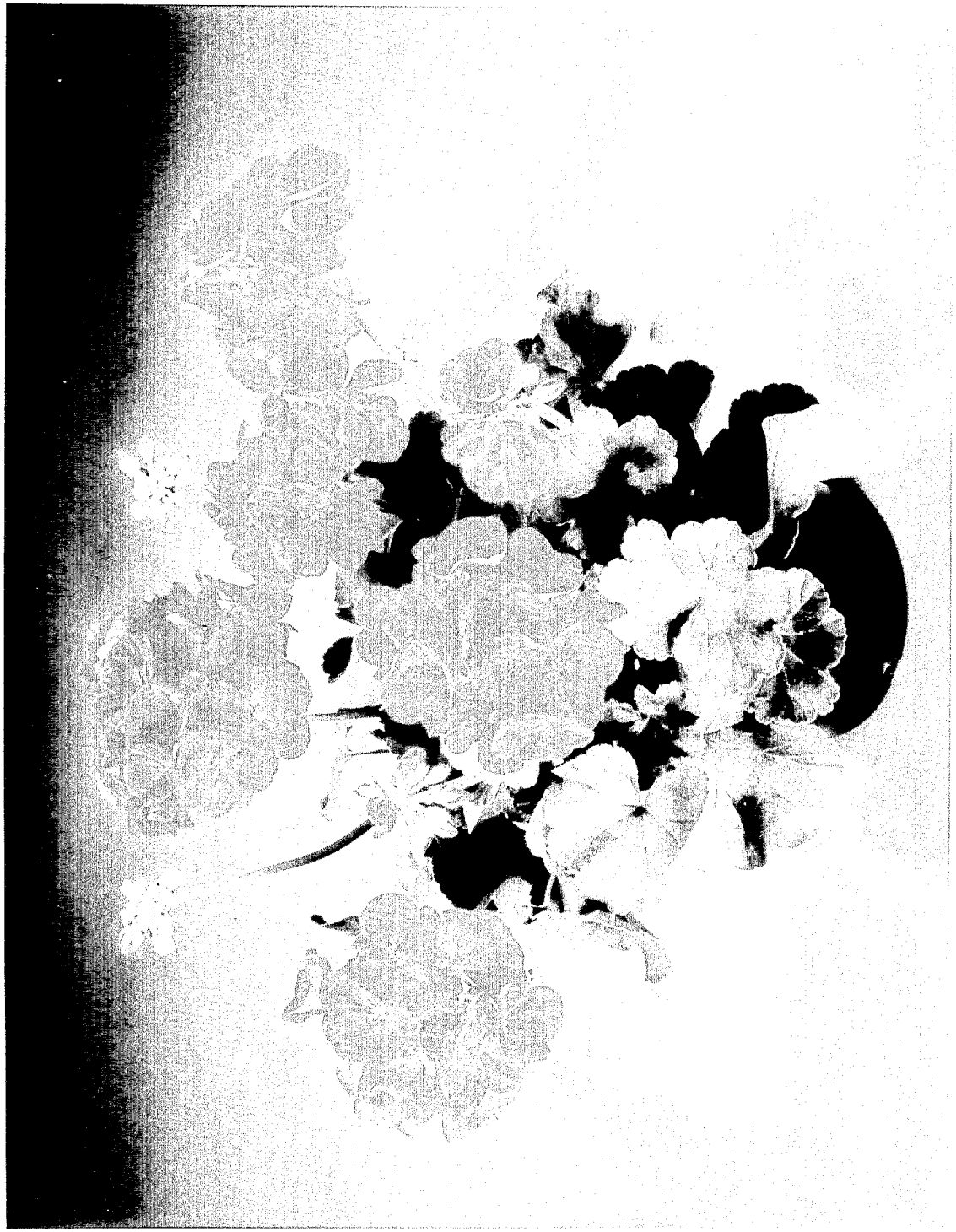

* * * * *